United States Patent

Davey et al.

[11] Patent Number: 6,054,311
[45] Date of Patent: Apr. 25, 2000

[54] RECOVERING CRYOPRESERVED CELLS USING GASSED POLYFLUORINATED COMPOUNDS

[75] Inventors: Michael Raymond Davey; Kenneth Charles Lowe; John Brian Power, all of Nottingham, United Kingdom

[73] Assignee: F2 Chemicals Limited, United Kingdom

[21] Appl. No.: 08/981,204

[22] PCT Filed: Jun. 13, 1996

[86] PCT No.: PCT/GB96/01432

§ 371 Date: Dec. 18, 1997

§ 102(e) Date: Dec. 18, 1997

[87] PCT Pub. No.: WO97/00943

PCT Pub. Date: Jan. 9, 1997

[30] Foreign Application Priority Data

Jun. 20, 1995 [GB] United Kingdom ............ 9512529

[51] Int. Cl.[7] .................... C12N 1/00; C12N 1/04; C12N 5/00
[52] U.S. Cl. .............. 435/260; 435/243; 435/248; 435/374; 435/395; 435/397; 435/401; 435/402; 435/404; 435/410; 435/420
[58] Field of Search .................. 435/325, 374, 435/395, 397, 401, 402, 410, 420, 243, 248, 252.1, 260, FOR 100, FOR 104, FOR 114

[56] References Cited

U.S. PATENT DOCUMENTS 4,251,995  2/1981  Pert et al. ..................... 62/60
4,464,337  8/1984  Zelman ........................ 422/41
5,326,356  7/1994  Della Valle et al. ............ 623/15
5,650,164  7/1997  Della Valle et al. ............ 424/422
5,658,331  8/1997  Della Valle et al. ............ 623/15

FOREIGN PATENT DOCUMENTS 0 033 402    8/1981  European Pat. Off. .
WO 93/02653  2/1993  WIPO .
WO 94/21116  9/1994  WIPO .

OTHER PUBLICATIONS

Urushihara et al, "A Comparison Study of Rat Pancreas Preservation Using Perflurochemical . . . " BIOMAT pp. 933–936, 1992.

Kuroda et al, "The Mechanism of Action of the Two–Layer (Euro–Collins Solution/Perflurochemical) Cold–Storage Method . . . " Transplantation vol. 53, pp. 992–994 #5. XP000578436, May 1992.

Kuroda et al, "Mechanism of Oxygenation of Pancreas During Preservation By A Two–Layer (Euro–Collins, Solution/Perflurochemical) Cold . . . " vol. 49, 694–96 #4, Apr. 1990.

Kohe J. Med. Sci., Sakai et al "A Novel Syst. for Sm. Bowel Pres. . . . " vol. 41, 33/46 pp. 33–46, Jun. 1995.

*Primary Examiner*—David M. Naff
*Assistant Examiner*—Deborah K. Ware
*Attorney, Agent, or Firm*—Nixon & Vanderhye

[57] ABSTRACT

After the cryopreservation of living cells, the cells in a post-thaw recovery stage are supported by a gas permeable medium. This medium comprises at least one polyfluorinated compound. This compound may be gassed, for example with oxygen where oxygenation is required.

12 Claims, No Drawings

RECOVERING CRYOPRESERVED CELLS USING GASSED POLYFLUORINATED COMPOUNDS

The present invention relates to a method of treatment of living cells, in particular a method of cryopreservation.

BACKGROUND OF THE INVENTION

Cryopreservation provides a means for the stable, long-term storage of biological plant and/or animal and/or microbial cells, tissues or organs, including plant zyotic or somatic embryos and meristems at ultra-low temperatures, eg 77° K. (−196° C.). For example, such a technique circumvents reduced morphological competence (totipotency), genetic change and secondary product formation of plant cell cultures associated with long-term culture at normal growth temperatures.

Cryopreservation comprises many steps, of which controlled freezing is only one; successful recovery is dependent on the combined effects of cryogenic and pre- and post-freeze treatments. The transition of tissues between low and physiologically normal temperatures and oxygen tensions causes respiratory imbalances which stimulate the production of toxic oxygen radicals as described for example by Fuller, B J, Gower, J D and Green, C J in "Free radical damage and organ preservation: fact or fiction", Cryobiology," 25, 377–393 (1988).

Physiological investigations of cryopreserved cells have shown that respiratory impairment occurs primarily, but not exclusively, during early post-freeze thaw recovery as described for example by Cella R, Colombo R, Galli M G, Nielsen M G, Rollo F and Sala F in "Freeze-preservation of rice cells: a physiological study of freeze/thawed cells", Physiologia Plantarum 55, 279–284 (1982).

It is an object of the present invention to provide a method for the recovery of living cells which have been subjected to cryopreservation in which the aforementioned respiratory impairment is reduced, whereby normal cell growth and function is promoted.

SUMMARY OF THE INVENTION

According to the present invention there is provided a method for the recovery of living cells which have been subjected to cryopreservation which comprises thawing the cells and then supporting them in a gas permeable medium comprising at least one polyfluorinated compound.

DESCRIPTION OF THE INVENTION

The polyfluorinated compound is preferably gassed, eg with oxygen where oxygenation is required.

The living cells to be treated by the method according to the present invention may comprise plant and/or animal and/or microbial cells. The cells may be present as individual cells, cell cultures, tissues, meristems, differentiated organs (eg floral parts), specialized cells (eg pollen grains) or subcellular components (eg protoplasts).

The living cells may advantageously be maintained in contact with a medium comprising an oxygenated polyfluorinated compound during other stages of the cryopreservation process in addition to the post-thaw recovery stage, for example during the cryoprotection, freezing and storage, recovery and post-recovery establishment of growth stages as described below.

The polyfluorinated compound may comprise a hydrocarbon in which at least 50 per cent of the hydrogen atoms have been substituted by fluorine atoms. The polyfluorinated compound desirably is a perfluorocarbon or derivative thereof collectively referred to herein as "PFCs". Particularly preferred polyfluorinated compounds for use in the method according to the present invention include perfluorocarbons such as perfluoroalkanes, perfluoro(alkylcycloalkanes), perfluoro(alkylsaturated heterocyclics) and perfluoro(tert-amines) or mixtures thereof. These compounds are capable of absorbing large amounts of oxygen and other respiratory gases and are substantially inert and non-toxic. Inert additives, eg thickeners or gels, eg silicones may be added to the perfluorocarbon(s). Examples of suitable PFCs include perfluorodecalin, perfluorophenanthrene, perfluorooctyl bromide, perfluorobutyltetrahydrofuran and perfluorotributylamine.

PFCs can dissolve substantial volumes of respiratory gases and beneficially enhance, for example, oxygen supply to cells. The use of a support medium which comprises one or more polyfluorinated compounds such as PFCs therefore beneficially improves the efficacy of the cell cryopreservation process, especially of the post-thaw recovery stage, as exemplified below.

Cells which are to be treated by the method according to the present invention may during freezing and storage, eg under liquid nitrogen, be contained in a cryoprotectant medium, eg an aqueous nutrient containing liquid containing cryoprotectants such as one or more of glycerol, dimethyl sulphoxide, sucrose, and proline and preferably oxygenated for plant cells, but for other living cells (such as microbial systems) and, depending on their aerobic or anaerobic respiratory requirements, the PFC should be gassed as appropriate (eg with carbon dioxide, ethylene, etc.).

Suspensions of cell cultures to be frozen and stored may be prepared by addition of an osmotically active molecule into the culture medium to provide partial dehydration of the cells in the aqueous liquid. This addition is preferably made over a period of time, eg greater than one day, preferably more than three days, before freezing.

When it is required to thaw the cells after storage a container, containing the cells in cryoprotectant medium, may be plunged into a liquid, eg sterile water, at a suitable temperature elevated above room temperature, eg 30° C. to 50° C., especially 40° C. to 45° C., and removing excess cryoprotectants by separation in the liquid.

Following the thaw stage, the cells are treated in a post-thaw recovery stage. In this stage the cells are supported in one of the ways described below to be in contact with a suitable aqueous nutrient-containing medium, which may be a gel or semi-solid, and also in contact with one or more polyfluorinated compounds, eg PFCs.

Liquid, gassed PFC may be underlaid, in relation to the nutrient-containing solution (liquid or gelled), at the various stages of addition in an appropriate containment vessel (eg a vial).

Where the cells are plant cells, the post-thaw recovery stage is desirably carried out in the dark to prevent cell damage.

Fresh aqueous medium and fresh PFC are desirably supplied on one or more occasions part-way through the recovery stage.

The volume of PFC required at the various stages of cryopreservation could be species-specific, but ratios of 1:1 (v:v) to at least 5:1 (v:v) of PFC:nutrient-containing solution (liquid or gelled,) may be appropriate to enhance effective cryopreservation.

Following a suitable recovery stage, cells may be re-initiated in a hydrated liquid growth medium as used for unfrozen cells, with the option of further contact with an oxygenated PFC.

As noted above, the living cells in the post-thaw recovery stage are desirably supported and in contact with an aqueous medium and one or more PFCs. Support may be provided by a solid, porous medium or the like, eg a filter, sieve or grille, or by a semi-solid or gel formed from the aqueous medium. Such a semi-solid or gel may form a base layer on which the cells are deoosited. Alternatively, the cells may be deposited on a PFC base layer and overlaid with a semi-solid or gel aqueous layer.

Alternatively, the cells may be encapsulated in semi-solid or gel beads or droplets.

The PFC may be incorporated as droplets or microdroplets in a suspension in the aqueous medium which may be formed into a semi-solid or gel layers, beads etc.

In the post-thaw recovery stage, in the method according to the present invention the medium in contact with the cells to be treated desirably includes an aqueous phase which may, dependent upon the cell type or species, comprise a hydrated gel. A gel is a substance that is prepared as a colloidal solution and that will, or can be caused to, form a semi-solid material. Such gels may be prepared by first dissolving in water or aqueous solvent as continuous phase a hydrophilic polymeric substance (serving as a solute or disperse phase) that, upon curing or setting, combines with the continuous phase to form a semi-solid material. In other words, the water becomes homogeneously associated with the solute molecules without experiencing any substantial separation of the continuous phase from the disperse phase. However, water molecules can be freely withdrawn from a cured hydrated gel, such as by evaporation. When cured, these gels have the familiar characteristic of compliant solids, like a mass of gelatin, where the compliance becomes progressively less and the gel becomes more solid to the touch as the relative amount of water in the gel is decreased.

In addition to being water-soluble, suitable gel solutes are neither cytotoxic nor substantially phytotoxic. As used herein, a "substantially non-phytotoxic" substance is a substance that does not interfere substantially with normal cell development, such as by killing a substantial number of cells, substantially altering cellular differentiation or maturation, causing mutations, disrupting a substantial number of cell membranes or substantially disrupting cellular metabolism, or substantially disrupting any other process.

Suitable gel solutes include, but are not limited to, the following: sodium alginate, agar, agarose, amylose, pectin, dextran, gelatin, starch, amylopectin, modified celluloses such as methylcellulose and hydroxyethylcellulose and polyacrylamide. Other hydrophilic gel solutes can also be used, so long as they possess similar hydration and gelation properties and lack of toxicity. Also, it is important to be able to add other substances such as nutrients or emulsified materials to the gel without substantially interfering with gelling ability. Further, a cured gel should have sufficient strength to maintain the integrity of the biological cells, tissues or organs (embryo) material without the material being excessively durable.

Gels are typically prepared by dissolving a gel solute, usually in fine particulate form, in water or aqueous solvent to form a gel solution. Depending upon the particular gel solute, heating is usually necessary, sometimes to boiling, before the gel solute will dissolve. Subsequent cooling will cause many gel solutions reversibly to become gelled. Examples include gelatin, agar, and agarose. Such gel solutes are termed "reversible" if reheating cured gel will re-form the gel solution. Solutions of other gel solutes require a complexing agent which serves to cure the gel chemically by crosslinking gel solute molecules. For example, sodium alginate is cured by adding calcium nitrate ($Ca(NO_3)_2$) or salts of other divalent ions such as, but not limited to, calcium, barium, lead, copper, strontium, cadmium, zinc, nickel, cobalt, magnesium and iron to the gel solution. Many of the gel solutes requiring complexing agents become irreversibly cured, where reheating will not re-establish the gel solution.

The concentration of gel solute required to prepare a satisfactory gel for use in the method according to the present invention varies depending upon the particular gel solute. In general, a solute concentration of less than 2.5% (w/v) is suitable.

The gel solution preferably includes cell nutrients and other beneficial substances such as vitamins and a source of carbon and energy (herein collectively termed generally "nutrients") and one or more growth regulators (phytohormones). Typical ways of providing nutrients are to dissolve the gel solute in a solution of the nutrients or to add a volume of concentrated nutrient solution to the gel solution before curing the gel. In this way, when the gel sets any areas of the cells in contact with the gel may also be in direct contact with nutrient solutes, where the nutrient solutes are present in substantially uniform concentrations throughout the gel. Another way to provide nutrients to the cells is to place a gel capsule containing the cells but lacking nutrients in contact with a second mass of the same of a different type of hydrated gel which does contain nutrients.

Because PFCs are non-polar they are not miscible with aqueous liquid media and the aforementioned gel solutions. In order to combine a sufficient amount of a PFC with an aqueous gel solution to be useful as an oxygen absorber or carrier, it may be convenient to create a suitable stable emulsion of the PFC. In such an emulsion, microdroplets of the PFC, comprising the disperse phase, may be uniformly suspended in the gel solution (the continuous phase). As used herein, a "suitably stable" emulsion is one in which the disperse phase remains suspended in the continuous phase.

Another possible way to provide nutrients is to place a gel unit containing the cells but lacking nutrients in contact with a second unit comprising microencapsulated nutrient or nutrients associated with any substantially non-phytotoxic substance that will allow the cell-containing gel unit. Representative materials include, but are not limited to, water, a gel similar to the gel in the embryo-containing unit, vermiculite, perlite, or any polymeric material that is non-toxic and will release the nutrients readily over a suitable period of time.

A number of possible nutrient formulations exist in the prior art, including a number of proprietary formulations. Of course, when preparing a liquid nutrient medium or adding such a nutrient solution to a gel solution, the concentrations of both solutions should be high enough such that the resulting mixture of the two solutions has the proper concentrations of gel and nutrients.

The nutrient solution can also include cell growth hormones and other compounds serving to further increase the probability of cell survival, post thaw recovery and subsequent mitotic division.

Since nutrient media, nutrient liquids, and any nutrient-containing gel is a rich growth medium for micro-organisms and fungi, it is important that all such liquids, as well as the cells' media themselves, be sterile before use. Cells, and their associated culture medium including any PFC-based supplementation are kept sterile during subsequent growth by culturing under sterile conditions. Liquids can be autoclaved, microfiltered or irradiated, while appropriate containment (culture) vessels may be autoclaved, irradiated or subjected to an appropriate disinfectant (chemical) treatment.

In order to stabilize the aqueous phase/PFC suspension, a surfactant can be utilized. The suspension can also be suitably stabilized in some instances merely by curing the gel.

Although a number of different types of surfactants would be effective in stabilizing an emulsion of PFC, the surfactant must be non-toxic to the cells.

Emulsion microdroplets can be created by various methods known in the art, including using a high-shear mixing apparatus or via ultrasonic means to mix the aqueous and PFC phases. In the case of ultrasonic devices, more ultrasonic energy must be introduced into the liquid mixture to achieve smaller microdroplet sizes. Representative ranges of microdroplet sizes are from about 100 $\mu$m diameter to less than 1 $\mu$m. In general, the smaller the microdroplet size, the more efficient the oxygen absorption and transport through the gel, since suspensions of smaller microdroplets have a larger total microdroplet surface area than suspensions of larger microdroplets. However, as a result of their greater surface area, suspensions of smaller microdroplets require more surfactant to render them suitably stable than emulsions of larger microdroplets.

Generally, the PFC concentration in a gel is about 25% (w/v) or less. The preferred concentration range of PFC in a gel is up to about 15% (w/v). The optimal range will depend in part on the type of gel solute, the oxygen-carrying capability of the particular PFC, the size of the emulsion microdroplets, and the desired oxygen concentration in a gel.

Embodiments of the present invention will now be described by way of example only.

The following procedures were carried out using rice as a model but similar procedures may be applied to other plant, animal or microbial cell systems irrespective of origin or species.

Cell suspension cultures of Japonica rice (*Oryza sativa* L.) cv. Taipei 309 were initiated from embyogenic callus derived from mature seed scutellum (as described by Finch, R P, Lynch, P T, Jotham, J P and Cocking E C in "Isolation, culture and fusion of rice protoplasts", in Bajaj YPS (Ed), Biotechnology in Agriculture and Forestry, Vol 14 Springer-Verlag, Heidelberg, pp 251–268) (1991).

Suspensions were routinely maintained in liquid AA2 medium (an example of an aqueous nutrient-containing liquid medium as described by Abdullah, R, Thompson, J A and Cocking, E C in "Efficient plant regeneration from rice protoplasts through somatic embryogenesis", Bio/Technology, 4 1087–1090 (1989)).

The cell suspension was contained in 100 ml Erlenmeyer flasks, on a rotary shaker (125 rpm) in the dark at a temperature of 28° C. Partial dehydration of the cells was achieved by the incorporation of osmotically active molecules such as mannitol into the culture medium. Cells were transferred to the liquid AA2 medium supplemented with 60 gl$^{-1}$ mannitol 3 to 4 days before freezing.

Cryoprotection Stage

Cells were harvested on a 30 $\mu$m nylon sieve and placed into 2 cm$^3$ polypropylene vials (Starstedt Ltd., Leicester, UK; 0.2 g of cells/vial). Approximately 0.75 ml of chilled (on ice water), filter sterilized, cryoprotectant mixture (glycerol, 46.0 gl$^{-1}$; dimethyl sulphoxide 39.0 gl$^{-1}$; sucrose 342.3 gl$^{-1}$; praline 5.0 gl$^{-1}$) was added to each vial and mixed with the cells. All cryoprotectants were AnalaR (TM) grade, with exception of dimethyl sulphoxide which was spectroscopically pure. The cryoprotectant mixture was made up in liquid AA2 medium and the pH adjusted to 5.8. PFC can be incorporated by direct addition at this stage in ratios (PFC to cryoprotectant/nutrient solution) of 1:1 through to 1:20. PFC may be gassed or not dependent upon species and cell type.

Freezing and Storage Stages

Vials containing cells were transferred to (aluminum) canes and cryoprotected for 1h on iced water. Cells were frozen in a controlled rate freezer (eg Planer Cryo 10 series; Planer Biomed, Sunbury-on-Thames, Middlesex, UK) from 0° C. to −35° C. at a rate of −1° C. min$^{-1}$ and held for 30 min before transferring to liquid nitrogen (77° K) (−196° C.).

Thawing and Recovery Stages

The choice of media is species dependent. Thawing was performed, after storage in liquid nitrogen, by plunging the vials into sterile water maintained at a temperature of 40° C. to 45° C. Excess cryoprotectants (with or without PFC) were removed. The cells were placed onto two 2.5 cm filter paper discs (Whatman No. 1; one disc above the other, per bottle) overlying 5.0 ml aliquots of AA2 medium containing 0.4% (w/v) agarose (Sigma Type 1), in 100 ml glass, screw-capped bottles. Oxygenated PFC (25.0 ml) was then incorporated (within 30 min) as an underlay to the nutrient solution. Alternatively, 2.0 ml oxygenated PFC may be added to each well of a 24-well Repliplate (sterilized) upon which (per well) 1.0 ml of nutrient solution is added (within 30 min) followed by 20.0 mg of cells retained on the upper surface of two (13 mm) filter paper discs (Whatman No. 1) in turn placed on the surface of the nutrient solution.

Establishment of growth

The contents of one vial were placed in each bottle and the bottles were maintained at a temperature of 28° C. in the dark. Alternatively, the contents of one vial were used to prepare 10 wells of the 24-well Repliplates as appropriate. Cells, irrespective of the mode of culture for thawing and initial recovery, were subcultured, by transferring the uppermost filter paper disc (from bottle or Repliplate) to fresh AA2 medium, after 4 days. Oxygenated PFC was then incorporated as before, dependent on culture method. A portion of cells was taken to investigate viability and metabolic capacity using triphenyl tetrazolium chloride (TTC) as described by Steponkus, P L and Lamphear, F O in "Refinement of the triphenyl tetrazolium chloride method of determining cold injury" Plant Physiology. 42, 1423–1426 (1967). The TTC assay is dependent on dehydrogenase reduction of TTC to produce formazan, which can be measured spectrophotometrically.

All manipulations during the recovery stage were performed in the dark as appropriate, thereby reducing photo-oxidation damage to the cells. Suspensions were re-initiated in liquid AA2 medium, 14 days after thawing and maintained under the same conditions as unfrozen cultures. Oxygenated PFC could then be further incorporated, at this stage as a media supplement.

Investigations have shown that cryopreserved rice cells can be successfully recovered in the presence of perfluorodecalin (the commercial product Flutec® PP6 (TM) manufactured by the present applicants), using the aforementioned recovery and early culture phases, which involves overlaying semi-solid AA2 medium onto oxygenated perfluorocarbon.

Basic Findings

Embryogenic rice cells were recovered from cryopreservation using standard protocols as control. Rice cells cultured on the surface of semi-solid culture medium overlying oxygenated PP6 in 100 ml bottles as described hereinbefore. Cultures were incubated for three days and the viability of the cells assessed using the TTC assay specified above.

The measured viabilities of cryopreserved rice cells with and without the presence of oxygenated perfluorodecalin as measured spectrophotometrically are given in Table 1: Cells recovered from PFC-enhanced cryopreservation exhibit normal growth kinetics.

TABLE 1

| Control (PP6 absent) (absorbance at 490 nm) | Oxygenated PP6 present (absorbance at 490 nm) |
|---|---|
| 0.316 | 0.398 |
| 0.463 | 0.361 |
| 0.264 | 0.469 |
| 0.354 | 0.384 |
| 0.227 | 0.379 |
| 0.257 | 0.418 |
| 0.689 | 0.451 |
| 0.327 | 0.485 |
| 0.364 | 0.356 |
| 0.424 | 0.570 |
| 0.252 | 0.477 |
| 0.281 | 0.487 |
| 0.319 | 0.616 |
| 0.371 | 0.381 |
| 0.394 | 0.388 |
| 0.416 | 0.274 |
| 0.398 | 0.435 |
| 0.366 | 0.438 |
| 0.262 | 0.470 |
| 0.511 | 0.508 |

Cryopreserved rice cells (of Accession 97) cultured in the presence of oxygenated perfluorodecalin PP6 were found to be significantly ($p<0.05$) more viable ($0.4458\pm0.07$) than control treatments lacking perfluorocarbon ($0.3456\pm0.078$) based on a sample size of 20 replicates as illustrated in Table 1.

Comparably significant results have been obtained with rice, Accession 14/R2 as handled for bottle culture and/or Repliplate culture.

What is claimed is:

1. A method for recovering living cells which have been subjected to cryopreservation comprising the steps of:

(1) thawing said cells;

(2) supporting said cells in a gas permeable medium comprising at least one polyfluorinated compound gassed with a respiratory gas for said cells; and (3) recovering said cells from said medium.

2. The method according to claim 1 wherein said cells are selected from the group consisting of plant cells, animal cells and microbial cells.

3. The method according to claim 1 wherein the living cells prior to cryopreservation are in contact with said medium containing at least one polyfluorinated compound.

4. The method according to claim 1 wherein the polyfluorinated compound is a perfluorocarbon compound.

5. The method according to claim 1 wherein during cryopreservation the living cells are contained in a cryoprotectant medium.

6. The method according to claim 1 wherein a culture medium containing the living cells is partially dehydrated prior to the freezing stage of the cryopreservation.

7. The method according to claim 1 wherein the thawing step (I) is carried out by plunging the medium containing the living cells into a sterile liquid at elevated temperature and removing excess cryoprotectant in the liquid.

8. The method according to claim 1 wherein following thawing in step (1) the cells are supported in step (2) in contact with an aqueous nutrient containing solution and said gas permeable medium comprising at least one polyfluorinated compound.

9. The method according to claim 8 wherein said gas permeable medium in step (2) is a solid porous medium comprising a filter, sieve or grille.

10. The method according to claim 8 wherein said gas permeable medium is a semi-solid or gel formed from the aqueous medium.

11. The method according to claim 8 wherein additional aqueous medium and polyfluorinated compound are added to the medium supporting the living cells at least once during the recovery method.

12. The method according to claim 8 wherein the ratio of said at least one polyfluorinated compound to said aqueous nutrient-containing solution is in the range, by volume, of from 1:1 to 5:1.

* * * * *